United States Patent [19]

McClure et al.

[11] 4,056,578
[45] Nov. 1, 1977

[54] ISOPARAFFIN-OLEFIN ALKYLATION PROCESS USING A SUPPORTED PERFLUORINATED POLYMER CATALYST

[75] Inventors: James D. McClure; Stanley G. Brandenberger, both of Houston, Tex.

[73] Assignee: Shell Oil Company, Houston, Tex.

[21] Appl. No.: 783,522

[22] Filed: Apr. 1, 1977

Related U.S. Application Data

[62] Division of Ser. No. 663,956, March 4, 1976, Pat. No. 4,038,213.

[51] Int. Cl.$^2$ .............................................. C07C 3/54
[52] U.S. Cl. ............................................... 260/683.47
[58] Field of Search ...................... 260/683.47, 683.58, 260/683.44, 683.63

[56] References Cited

U.S. PATENT DOCUMENTS

| 2,843,642 | 7/1958 | Kelly | 260/683.44 |
| 3,116,346 | 12/1963 | Van Dyke | 260/683.63 |
| 3,960,764 | 6/1976 | Bernard et al. | 260/683.47 |
| 4,022,847 | 5/1977 | McClure | 260/683.47 |

FOREIGN PATENT DOCUMENTS 733,753   7/1955   United Kingdom ............ 260/683.58

Primary Examiner—George Crasanakis
Attorney, Agent, or Firm—Dean F. Vance

[57] ABSTRACT

Alkylation of an isoparaffin with an olefin is carried out at a reaction temperature of 80°-225° C with a solid perfluorinated polymer catalyst containing pendent sulfonic acid groups and supported on an inert porous carrier having an average pore diameter of between 50-600A.

8 Claims, No Drawings

ISOPARAFFIN-OLEFIN ALKYLATION PROCESS USING A SUPPORTED PERFLUORINATED POLYMER CATALYST

This is a division of application Ser. No. 663,956, filed Mar. 4, 1976 which issued as U.S. Pat. No. 4,038,013.

BACKGROUND OF THE INVENTION

Hydrocarbon conversion and the isomerization of hydrocarbons in particular, is of special importance to the petroleum industry. In recent years, with the advent of catalytic converters in automobiles and the required use of non-leaded gasoline, a need has arisen for higher octane number gasolines. Natural straight-run gasolines, i.e., naphthas, contain, chiefly, normal paraffins, such as normal pentane and normal hexane, which have relatively low octane numbers. It has become essential, therefore, to convert these low octane components to their higher octane counterparts. The isomerization of these hydrocarbon components accomplish this conversion, i.e., the isomers resulting have a much higher octane rating. Hence, the facility with which this isomerization is accomplished has become of prime importance.

Likewise, the need for isoparaffins, benzene, xylene, and ethyl benzene as building components in the petrochemical industry is increasing. Accordingly, the need for improved hydrocarbon conversion processes in the petrochemical industry is also great.

One of the primary hydrocarbon conversion processes now employed is the alkylation of isoparaffins. It was thought that certain sulfonated fluorocarbon polymers possess sufficient activity and stability to be useful as alkylation catalysts. However, in a recent study by Kapura and Gates, Sulfonated Polymers as Alkylation Catalysts, Industrial Engineering Chemistry Product Research Development, Vol. 12, No. 1, pp. 62–66 (1973), it was found that a sulfonated fluorocarbon vinyl ether polymer was inactive in alkylating isobutane with propylene in the gas phase and in a mole ratio of 5 to 1 at 260° C. The conculsion reached in that study was that the sulfonated fluorocarbon vinyl ether polymer catalyst was too weakly acidic to catalyze paraffin alkylation and that the polymer was not a useful catalyst. That study also showed that these same ion exchange resins were useful in the alkylation of benzene with propylene in the vapor phase to form cumene. However, the conclusion reached by Kapura and Gates with regard to the formation of cumene was that the sulfonated polymer was not "a particularly useful catalyst at temperatures greater than about 150° C." Contrary to the conclusions reached by Kapura and Gates, it has now been found that a supported perfluorinated polymer containing pendant sulfonic acid groups is a very active catalyst in the preparation of ethylbenzene from benzene and ethylene, in the alkylation of isoparaffins, in the isomerization of normal alkanes, and in the disproportionation of toluene.

SUMMARY OF THE INVENTION

The present invention comprises an improved hydrocarbon conversion process which comprises contacting said hydrocarbons under hydrocarbon converting conditions with a supported perfluorinated polymer catalyst containing a repeating structure selected from the group consisting of:

a) 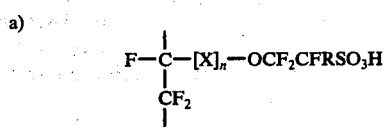

or b) 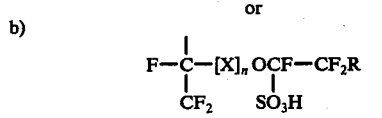

where n is 0, 1 or 2; R is a radical selected from the group consisting of fluorine and perfluoroalkyl radicals having from 1 to 10 carbon atoms; and X is selected from the group consisting of:

[O(CF$_2$)$_m$], [OCF$_2$CFY] or [OCFYCF$_2$]

where m is an integer from 2 to 10 and Y is a radical selected from the class consisting of fluorine and the trifluoromethyl radical.

Also disclosed is a novel catalyst composition for the conversion of hydrocarbons which comprises a catalytic component dispersed on a solid, porous support. The catalyst component is the perfluorinated polymer having the structure I or II above. The solid porous support has an effective pore diameter of between about 50 A and about 600 A and is preferably selected from the group consisting of alumina, silica, silica-alumina and porous glass.

DETAILED DESCRIPTION OF THE INVENTION

A. The Catalyst Composition

The catalyst employed in the present invention is a solid at reaction conditions. The catalyst broadly comprises a perfluorinated polymer having acid groups in the amount of about 0.01 to 5 mequiv/gram catalyst. Preferably, the polymer contains about 0.05 to 2 mequiv/gram of catalyst.

In a specific embodiment, the polymer catalyst contains a repeating structure selected from the group consisting of:

a) 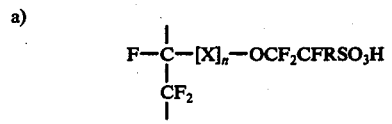

or b) 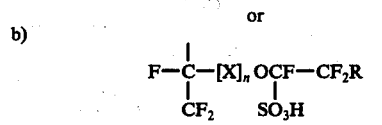

where n is 0, 1 or 2; R is a radical selected from the group consisting of fluorine and perfluoroalkyl radicals having from 1 to 10 carbon atoms; and X is selected from the group consisting of:

[O(CF$_2$)$_m$], [OCF$_2$CFY] or [OCFYCF$_2$]

where m is an integer from 2 to 10 and Y is a radical selected from the class consisting of fluorine and the trifluoromethyl radical. In a preferred embodiment, n is 1 to 2, Y is a trifluoromethyl radical, R is fluorine, and m is 2. Catalyst of the above-noted structure typically have a molecular weight of between about 1,000 and 500,000 daltons.

Polymer catalysts of the above-noted structure can be prepared in various ways. One method, disclosed in Connolly et al, U.S. Pat. No. 3,282,875 and Cavanaugh et al, Pat. No. 3,882,093, comprises polymerizing vinyl compounds of the formula:

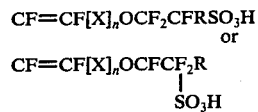

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from $-50°$ to $+200°$ C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to prepare catalysts for the present invention by copolymerizing the vinyl ethers of structure III or IV with perfluoroethylene and/or perfluoroalpha-olefins. A preferred copolymer prepared by polymerizing perfluoroethylene with a perfluorovinyl ether containing attached sulfonic acid groups would have the following structure:

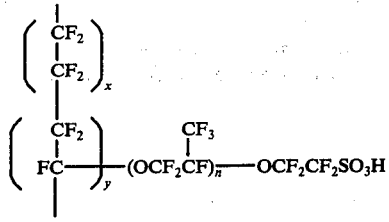

wherein $n = 1$ or 2 and the ratio of $x$ over $y$ varies from about 2 to about 50. The polymer of structure V is available commercially under the tradename of NAFION ® resin. Catalysts of the above-noted structure V offer the advantages of high concentrations of accessible acid groups in a solid phase.

The catalyst of the present invention is supported on a porous solid inert support. The supported catalysts possess greater activity per unit of acid present than do the unsupported catalysts. By porous solid support is meant an inert support material having a porous structure and an average pore diameter of between about 50 A and about 600 A or higher. Preferably, the average pore diameter of the support is greater than about 200 A. The porous solid support of the subject invention is preferably selected from the inorganic oxide group consisting of alumina, fluorided alumina, zirconia, silica, silica-alumina, magnesia, chromia, boria, and mixtures and combinations thereof. Other porous solid supports may also be used such as bauxite, kieselguhr, kaolin, bentonite, diatomaceous earth and the like. Other porous solid supports such as polytetrafluoroethylene, carbon, e.g., charcoal, polytrichlorofluorofluoroethylene, porous glass, and the like may also be used. Basically, the support should be substantially inert to the catalyst, and be insoluble in the mixture under reaction conditions.

The average pore diameter (also known as effective pore diameter) of the support, which is related to the ratio of pore volume to surface area, is an important consideration in the choice of support. Generally, as the average pore diameter of the support is increased, the activity of the catalyst is increased. For example, as shown in the Illustrative Embodiments which follow, an isomerization catalyst composition having a porous glass support with a 207 A average pore diameter was only about 60% as active as an isomerization catalyst composition having a porous glass support with a 310 A average pore diameter. Most preferably, the support should possess both a high surface area and a high average pore diameter.

The weight ratio of catalyst to support varies from about 0.1:100 to about 30:100, preferably from about 1:100 to about 15:100. The support is preferably impregnated with the catalyst by dissolving the catalyst in a solvent, such as ethanol, mixing the support and the catalyst solution, and then drying the impregnated support under vacuum at a temperature of between about 25° C and about 100° C so as to remove the solvent.

The invention is further defined with reference to a variety of particular hydrocarbon conversion processes.

B. Alkylation of Isoparaffins

The catalytic alkylation of paraffins involves the addition of an isoparaffin containing a tertiary hydrogen to an olefin. The process is extensively used by the petroleum industry to prepare highly branched paraffins mainly in the $C_7$ to $C_9$ range, which are high quality fuels for ignition engines. The overall process as to chemistry is a composite of complex reactions, and consequently a rigorous control of operating conditions and of catalyst is needed to assure predictable results.

Acid catalyzed hydrocarbon conversion processes comprising contacting an alkane with an olefin are well known. The reactants are generally contacted in the liquid phase and within a broad temperature range of about $-100°$ F to about $100°$ F with an acid catalyst such as, for example, sulfuric acid, fluorosulfuric acid or a halogen acid, such as hydrofluoric acid. Typical alkylation processes are disclosed in U.S. Pat. No. 2,313,103, U.S. Pat. No. 2,344,469, U.S. Pat. No. 3,864,423 and British Pat. No. 537,589. Catalyst moderators, such as water and lower monoethers as disclosed in U.S. Pat. No. 3,887,635, are often employed to improve the selectivity of the catalyst.

The catalysts employed in the above-noted references are liquid catalysts. Therefore, the process equipment must be necessarily complex. The reaction zone typically contains elaborate hardware to ensure initmate mixing of catalyst and reactions. In addition, a separation chamber is required to separate the catalyst from the hydrocarbon product. Further, since the reaction typically takes place at lower than ambient temperature, refrigeration facilities are also a necessary part of the process.

One means to improve the alkylation process would be to employ a solid catalyst instead of a liquid catalyst.

However, conventional solid acid catalysts, such as zeolites, are not very stable in their catalytic activity. For example, during isobutane/butene-2 alkylation, zeolites undergo catastrophic decline in activity in 4 to 6 hours. Likewise, other solid alkylation catalysts, such an HF antimony pentafluoride catalyst as disclosed in U.S. Pat. No. 3,852,371, are not commercially stable catalysts.

In the present invention, a $C_4$ to $C_6$ isoparaffin containing a tertiary hydrocarbon or a hydrocarbon stream containing such isoparaffins is contacted with $C_2$ to $C_5$ monoolefin, mixtures thereof, or hydrocarbon streams containing such olefins, in the liquid phase and at a temperature of between about 80° C and about 225° C in the presence of the catalyst composition of the instant invention.

The present invention has a distinct advantage over the typical alkylation process in that the catalyst is a solid catalyst thereby eliminating many of the mixing, settling, separation, and neutralization problems associated with catalysts such as sulfuric acid, hydrofluoric acid, or fluoromethane sulfuric acid. The present catalyst is also superior to the other solid catalysts such as zeolites in that the present catalyst is very stable under reaction conditions. For example, catalyst runs with the instant catalyst of over 200 hours have been achieved with no appreciable decline in catalyst activity.

Further, contrary to prior investigations, the present catalyst is very active in the alkylation reaction resulting in over 90% conversion of the olefin and over 80% $C_8$ selectivity. In addition, the trimethylpentane selectivity (basis $C_8H_{18}$) of the present catalyst is over 75%.

As shown in the Illustrative Embodiments which follow, the supported catalysts have a much greater activity than do the unsupported catalyst based on the number of grams of catalyst present. For example, the activity of a 1% NAFION ® resin on a Johns Mahsville Chromosorb T is 2.5 times greater than a 5% Nafion resin on silica support and about 12 times greater than an unsupported Nafion resin catalyst per unit of actual catalyst present.

The olefin feed for the present invention contains olefins selected from the group consisting of $C_2$ to $C_5$ monoolefins and mixtures thereof. Examples of suitable olefins include propylene, isobutylene, butene-1, butene-2, trimethylethylene, the isomeric amylenes and mixtures thereof. In actual commercial use, however, these olefins will contain other hydrocarbons. The process of the instant invention contemplates the use of various refinery cuts as feedstocks. Thus, $C_3$, $C_4$ and/or $C_5$ olefin cuts from thermal and/or catalytic cracking units; field butanes which have been subjected to prior isomerization and partial dehydrogenation treatment; refinery stabilizer bottoms; spent gases; normally liquid products from sulfuric acid or phosphoric acid catalyzed polymerization and copolymerization processes; and products, normally liquid in character, from thermal and/or catalytic cracking units, are all excellent feedstocks for the present process.

The isoparaffin feed for the present invention comprises $C_4$ to $C_6$ isoparaffins containing tertiary hydrocarbon substituents, mixtures thereof, and hydrocarbon streams containing such components. A preferred isoparaffin is isobutane.

In order to prevent polymerization of the olefin, a large excess of isoparaffin is used. The weight ratio of isoparaffin to olefin varies from about 5:1 to about 1000:1, preferably about 20:1 to about 60:1. It has been found that when the isobutane to butene ratio is increased from 10:1 to 40:1, the $C_8$ selectivity and the total yield of greater than or equal to $C_5$ products are significantly increased while the yield of $C_{11}$–$C_{12}$ and $C_{14}$–$C_{16}$ products are decreased.

The process may be carried out either as a batch or continuous type of operation, although it is preferred to carry out the process continuously. It has been generally established that in alkylation processes, the more intimate the contact between the feedback and the catalyst, the better the yield of saturated product obtained. With this in mind, the present process, when operated as a batch operation, is characterized by the use of vigorous mechanical stirring or shaking of the reactants and catalyst.

When employing a continuous process, the feedstreams may be contacted with the supported catalyst in any suitable reactor. In one embodiment, the supported catalyst is packed in a vertical, tubular reactor bed with inert supports, such as ceramic balls or silicon carbide, above and below the supported catalyst to prevent entrainment of the solid catalyst. In a further embodiment, the supported catalyst is mixed with an inert material, such as quartz, and loaded in the reactor so as to improve the fluid dynamics of the system. The flow of the reactant feed stream may be upflow or downflow, with an upflow arrangement being preferred to ensure liquid phase alkylation.

Reaction temperature is varied between about 80° C and about 225° C depending upon the type of products desired. The reaction temperature must be kept below a about 225° C due to the lack of stability of the catalyst at temperatures of over 250° C. A preferred temperature range is between about 80° C and about 130° C. In general, the activity of the catalyst is greater at the higher temperatures. That is, as temperature increases, the conversion of olefin increases.

In general, the pressure in the alkylation reaction zone is maintained to keep the reactants in the liquid phase, and accordingly, will vary with the reactants employed and the reaction temperatures. Typical reaction zone pressure varies from about 10 psig to about 2,000 psig.

The weight hourly space velocity effectively measures the catalyst concentration employed, and hence also measures the relative activity of the catalyst. Weight hourly space velocity (WHSV) is defined as the weight per hour of olefin feed divided by the weight of catalyst (not including support) employed. For non-supported catalyst, the WHSV varies between about 0.05 and about 1.0, preferably about 0.15 and about 0.5 For a supported catalyst, the WHSV varies between about 0.5 to about 10.0. The larger WHSV employed for supported catalysts is possible because of the greater activity of the supported catalyst.

In a preferred embodiment, a gas stream is introduced into the reactor along with the olefin and isoparaffin feed streams. Typically, the gas is an inert gas such as nitrogen. However, it has been found that when the gas stream also contains hydrogen, the total yield of $C_5$ or greater products is increased without significantly increasing the n-butane selectively or changing the trimethylpentane selectivity. The effect of including this gas stream in the alkylation reaction is to improve the percentage of $C_8H_{18}$ in the $C_8$ product, which improvement most likely occurs via hydride transfer from hydrogen to an intermediate $C_8$ carbonium ion to give a $C_8H_{18}$ alkane.

The reaction products obtained are highly branched paraffins, mainly in the $C_5$ to $C_{12}$ range. The butenes produce mainly $C_8$ hydrocarbons, principally dimethylhexanes and trimethylpentanes, while isobutylene results in mainly trimethylpentanes. It is not necessary to neutralize the reaction products of the present invention, since little, if any, of the sulfonic acid groups on the catalyst are removed during the reaction.

The principal use of the alkylate produced according to the present invention is in the blending of motor gasoline. Alkylate is a preferred gasoline blending component because of its high octane number, which number is enhanced by the presence of high concentrations of $C_8$ hydrocarbons. Trimethylpentane is a particularly valuable alkylate component.

The invention is further illustrated by means of the following Comparative Example and Illustrative Embodiments which are given for the purpose of illustration only, and the invention is not to be regarded as limited to any of the specific materials or conditions recited therein.

In the Comparative Example and Illustrative Embodiments, the reactor employed was a 17 inch stainless steel tube equipped with both a liquid feed upflow inlet and a nitrogen inlet. The catalyst bed occupied about 10 inches in the center of the reactor; and on either side of the catalyst bed were packed about 10 grams of carborundum chips. The catalyst bed was initially charged with liquified isobutane at a flow rate of 10–20 milliliters per hour after the reactor was heated to 80°–120° C. Once the reactor was completely flooded with isobutane, the mixture of olefin and isoparaffin were charged to the reactor. In all cases, the olefin employed was 2-butene and the isoparaffin employed was isobutane.

In the Comparative Example and Illustrative Embodiments, the reactants were introduced in an upflow manner. Pressure in all cases was kept at 500 psig to maintain a liquid phase. In all cases, a 100% nitrogen was added to a rate of 0.3 liters per hour.

The products were recovered at periodic intervals and analyzed by gas chromatography. The percentage of alkenes in the $C_8$ fraction were determined by washing the fraction with 96% sulfuric acid to removed the alkenes.

In the Comparative Example and Illustrative Embodiments, the catalyst concentration is measured by weight hourly space velocity (WHSV, $hr^{-1}$) which is defined as the weight of the 2-butene feed per hour divided by the weight of catalyst employed. The weight of the support employed in the Illustrative Embodiments is not included in the calculation of WHSV. The total yield of greater than or equal to $C_5$ products is based on the weight of butene converted. Further, since 2,2,5-trimethylhexane is the only significant $C_9$ product formed and has a high octane number, it is included in the $C_8H_{18}$ fraction as reported.

COMPARATIVE EXAMPLE Ia

The catalyst for Comparative Example Ia was prepared by grinding Nafion XR granules with a blender to 150 micrometer or less particle size. The ground material was then treated twice with 30% sulfuric acid to convert the material from a potassium ($K^+$) form to the $H^+$ form. The treated material was collected by filtration, washed with distilled water until the washings were neutral, and then dried at 100° C and 3 mm pressure for 16 hours. The resulting catalyst contained about 0.85 milliequivalents of acid per gram of catalyst. The structure for the resulting catalyst is exemplified by the following repeating structure where $n = 1$ or 2 and the ratio of $x$ over $y$ varies from between 2 and about 50:

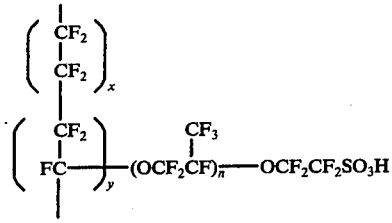

In Comparative Example $I^a$, the catalyst bed comprised 2.5 grams of catalyst plus 7.5 grams of quartz particles. The isobutane to butene-2 ratio was maintained to about 10 to 1, whereas the WHSV and temperature were varied as indicated. The total length of the run lasted over 90 hours, and the results are presented below in Tables 1a, 2a and 3a.

Table 1a

| Time, hrs | 3 | 5 | 7 | 9 | 11 | 13 | 15 | 16 | 18 | 19 | 20 | 22 |
|---|---|---|---|---|---|---|---|---|---|---|---|---|
| WHSV, hr | 0.4 | 0.4 | 0.4 | 0.4 | 0.4 | 0.66 | 0.66 | 0.66 | 0.66 | 0.66 | 0.66 | 0.66 |
| Temperature, °C | 100 | 100 | 100 | 100 | 100 | 100 | 100 | 100 | 100 | 100 | 100 | 100 |
| Butene Conversion, % | 97 | 97 | 97 | 98 | 99 | 96 | 96 | 96 | 95 | 95 | 95 | 96 |
| Total Yield ≥$C_5$'s, %w | 150 | 147 | 146 | 146 | 147 | 145 | 146 | 146 | 146 | 146 | 145 | 146 |
| Products, %w | | | | | | | | | | | | |
| $C_5$–$C_7$ | 3 | 3 | 2 | 2 | 2.5 | 2 | 2 | 2 | 1.5 | 2 | 2 | 1.5 |
| $C_8$–$C_9$ | 65 | 65 | 65 | 65 | 64 | 68 | 68 | 70 | 71 | 70 | 71 | 71 |
| $C_{11}$–$C_{12}$ | 20 | 20 | 22 | 22 | 20 | 20 | 19 | 17 | 17 | 17 | 16 | 19 |
| $C_{14}$–$C_{16}$ | 12 | 12 | 11 | 11 | 13.5 | 10 | 11 | 11 | 11 | 11 | 11 | 9.5 |
| Composition of $C_8$, % | | | | | | | | | | | | |
| $C_8H_{18}$ | 81 | 70 | 70 | 70 | 73 | 66 | 67 | 65 | 65 | 65 | 64 | 64 |
| $C_8H_{16}$ | 19 | 30 | 30 | 30 | 27 | 34 | 33 | 35 | 35 | 35 | 36 | 36 |
| Composition of $C_8H_{18}$, % | | | | | | | | | | | | |
| Trimethylpentanes | 75 | 75 | 70 | 71 | 63 | 67 | 70 | 71 | 74 | 66 | 66 | 67 |
| Dimethylhexanes | 18 | 18 | 19 | 20 | 24 | 20 | 21 | 20 | 19 | 24 | 22 | 23 |
| Methylheptanes | 4 | 4 | 6 | 5 | 6 | 6 | 4 | 4 | 4 | 5 | 6 | 5 |
| 2,2,5-Trimethylhexane | 4 | 4 | 5 | 5 | 7 | 7 | 5 | 5 | 3 | 5 | 6 | 5 |

Table 2a

| Time, Hr. | 24 | 26 | 28 | 30 | 32 | 33 | 34 | 36 | 38 | 39.5 | 42.5 | 44.5 | 46 |
|---|---|---|---|---|---|---|---|---|---|---|---|---|---|
| WHSV, hr.$^{-1}$ | 0.66 | 0.66 | 0.66 | 0.66 | 0.66 | 0.66 | 0.66 | 0.66 | 0.66 | 0.66 | 0.66 | 0.66 | 0.66 |
| Temperature, °C | 90 | 90 | 90 | 90 | 90 | 90 | 90 | 90 | 90 | 90 | 90 | 90 | 90 |
| Butene Conversion, % | 86 | 85 | 85 | 87 | 85 | 85 | 84 | 87 | 87 | 88 | 87 | 85 | 88 |
| Total Yield ≥$C_5$'s, %w | 142 | 140 | 140 | 140 | 139 | 139 | 140 | 143 | 140 | 142 | 138 | 139 | 141 |
| Products, %w | | | | | | | | | | | | | |
| $C_5$–$C_7$ | 3 | 2 | 1 | 2 | 1 | 1 | 2 | 1 | 1 | 1 | 2 | 1 | 1 |
| $C_8$–$C_9$ | 74 | 74 | 73 | 74 | 73 | 74 | 73 | 74 | 74 | 75 | 74 | 73 | 74 |
| $C_{11}$–$C_{12}$ | 14 | 16 | 17 | 16 | 15 | 16 | 14 | 16 | 16 | 14 | 16 | 17 | 15 |
| $C_{14}$–$C_{16}$ | 10 | 9 | 9 | 9 | 11 | 9 | 11 | 9 | 9 | 10 | 8 | 9 | 10 |
| Composition of $C_8$, % | | | | | | | | | | | | | |
| $C_8H_{18}$ | 56 | 58 | 56 | 58 | 56 | 57 | 60 | 58 | 57 | 56 | 57 | 57 | 58 |
| $C_8H_{16}$ | 44 | 42 | 44 | 42 | 44 | 43 | 40 | 42 | 43 | 44 | 43 | 43 | 43 |
| Composition of $C_8H_{18}$, % | | | | | | | | | | | | | |
| Trimethylpentanes | 75 | 74 | 75 | 75 | 74 | 75 | 74 | 73 | 75 | 73 | 74 | 75 | 75 |
| Dimethylhexanes | 18 | 18 | 17 | 17 | 18 | 19 | 17 | 19 | 17 | 19 | 17 | 19 | 18 |
| Methylheptanes | 3 | 4 | 4 | 4 | 4 | 4 | 5 | 4 | 5 | 5 | 5 | 4 | 4 |
| 2,3,5-Trimethylhexane | 4 | 4 | 4 | 4 | 4 | 2 | 4 | 5 | 3 | 3 | 4 | 2 | 3 |

Table 3a

| Time, hrs. | 50 | 52 | 56 | 58 | 60 | 66 | 70 | 72 | 90 |
|---|---|---|---|---|---|---|---|---|---|
| Temperature, °C | 90 | 90 | 80 | 80 | 80 | 80 | 90 | 90 | 90 |
| WHSV, hr$^{-1}$ | 0.33 | 0.33 | 0.33 | 0.33 | 0.33 | 0.33 | 0.33 | 0.33 | 0.33 |
| Butene Conversion, % | 95 | 95 | 76 | 73 | 70 | 68–72 | 91 | 94 | 95 |
| Total Yield ≧C$_5$'s | | 140 | 139 | 138 | 138 | 138 | 140 | 141 | 141 |
| Products, %w | | | | | | | | | |
| C$_5$–C$_7$ | | 1.5 | <1 | <1 | <1 | <1 | 1 | 1.5 | 1.6 |
| C$_8$–C$_9$ | | 68 | 78 | 78 | 80 | 81 | 68 | 68 | 70 |
| C$_{11}$–C$_{12}$ | | 18 | 13 | 15 | 13 | 11 | 19 | 19 | 17 |
| C$_{14}$–C$_{16}$ | | 13 | 9 | 6 | 7 | 7 | 12 | 11.5 | 12 |
| Composition of C$_8$, % | | | | | | | | | |
| C$_8$H$_{18}$ | | 60 | 50 | 49 | 48 | 50 | 58 | 58 | 56 |
| C$_8$H$_{16}$ | | 40 | 50 | 51 | 52 | 50 | 42 | 42 | 44 |
| Composition of C$_8$H$_{18}$, % | | | | | | | | | |
| Trimethylpentanes | | 75 | 83 | 80 | 80 | 80 | 75 | 75 | 74 |
| Dimethylhexanes | | 18 | 12 | 14 | 14 | 15 | 19 | 18 | 17 |
| Methylheptanes | | 4 | 3 | 3 | 3 | 3 | 4 | 4 | 5 |
| 2.2.5-Trimethylhexane | | 3 | 2 | 3 | 3 | 2 | 2 | 3 | 4 |

ILLUSTRATIVE EMBODIMENT Ia

The catalyst for Illustrative Embodiment Ia was prepared by impregnation of a silica gel support (Davison 57 with a 1.0 cc/g pore volume and 300 m²/g surface area) with an ethanol solution of Nafion XR granules. The ethanol was removed from the solid on a rotary evaporator leaving a 5% Nafion on silica catalyst. The structure of the resulting catalyst is exemplified by the repeating structure designated VI. About 5 grams of this catalyst was mixed with 5 grams of quartz to form the catalyst bed. The isobuane to butene-2 ratio was kept at 10:1 and the WHSV (based on the number of grams of Nafion resin present) was maintained at 3.3 hr$^{-1}$. The results along with the other operating conditions are presented below in Table 4a.

Table 4a

| Time, Hrs | 2 | 4 | 6 | 7 | 22.5 | 25.5 | 30.5 | 46.5 | 47.5 |
|---|---|---|---|---|---|---|---|---|---|
| Temperature, °C | 100 | 100 | 100 | 100 | 110 | 110 | 110 | 110 | 110 |
| Butene Conv., % | 74 | 73 | 70 | 65 | 70 | 69 | 68 | 71 | 70 |
| Total Yield C$_5$'s | — | 137 | 139 | — | 138 | 137 | 138 | 138 | 138 |
| Products, %w | | | | | | | | | |
| C$_5$–C$_7$ | | 2 | 2 | | 1 | 2 | 1.5 | 1 | 1.5 |
| C$_8$–C$_9$ | | 72 | 76 | | 73 | 72 | 74 | 75 | 76 |
| C$_{11}$–C$_{12}$ | | 20 | 16 | | 17 | 17 | 17 | 17 | 15 |
| C$_{14}$–C$_{16}$ | | 6 | 6 | | 9 | 9 | 6 | 7 | 7 |
| Composition of C$_8$,% | | | | | | | | | |
| C$_8$H$_{18}$ | | 51.5 | 51 | | 52 | 51.5 | 51 | 50 | 51 |
| C$_8$H$_{16}$ | | 48.5 | 49 | | 48 | 48.5 | 49 | 50 | 49 |
| Composition of C$_8$H$_{18}$,% | | | | | | | | | |
| Trimethylpentanes | | 74 | 76 | | 70 | 72 | 74 | 72 | 77 |
| Dimethylhexanes | | 19 | 17 | | 18 | 21 | 19 | 21 | 17 |
| Xethylheptanes | | 6 | 6 | | 8 | 6 | 6 | 6 | 5 |
| 2,2,5-Trimethylhexane | | 1 | 1 | | 4 | 1 | 1 | 1 | 1 |

ILLUSTRATIVE EMBODIMENT IIa

The catalyst for Illustrative Embodiment IIa was 1.1% Nafion on a fluoropolymer support and was prepared by adding dropwise 5 grams of a 5.5% solution of Nafion XR granules in ethanol to 20 grams of Chromosorb T (Johns-Manville teflon 6) support. After the ethanol was removed and the catalyst dried, it was determined that the catalyst contained 1.1% Nafion. The catalyst bed for Illustrative Embodiment II comprised 10 grams of the catalyst with no quartz being added. The catalyst structure is similar to that employed in Illustrative Embodiment Ia.

The operating conditions were 100° C, isobutane to butene-2 ratio of 10:1, and a WHSV (based on the number of grams of Nafion resin present) of 8.2 hr$^{-1}$. The results are presented below in Table 5a.

Table 5a

| Time, hrs. | 4 | 20 | 24 | 28 | 44 | 48 | 52 | 68 | 74 |
|---|---|---|---|---|---|---|---|---|---|
| Butene Conv., % | 65 | 70 | 70 | 71 | 65 | 65 | 65 | 68 | 65 |
| Total Yield C$_5$'s | — | 138 | 138 | — | 137 | 137 | — | 137 | 137 |
| Products, %w | | | | | | | | | |
| C$_5$–C$_7$ | — | 2 | 1 | — | 1 | 1 | — | 1 | 1 |
| C$_8$–C$_9$ | — | 76 | 76 | — | 74 | 74 | — | 76 | 79 |
| C$_{11}$–C$_{12}$ | — | 16 | 14 | — | 17 | 17 | — | 14 | 14 |
| C$_{14}$–C$_{16}$ | — | 6 | 9 | — | 8 | 8 | — | 9 | 6 |
| Composition of C$_8$,% | | | | | | | | | |
| C$_8$H$_{18}$ | — | 50 | 50 | — | 50 | 49 | — | 49 | 48 |
| C$_8$H$_{16}$ | — | 50 | 50 | — | 50 | 51 | — | 51 | 52 |
| Composition of C$_8$H$_{18}$,% | | | | | | | | | |
| Trimethylpentanes | — | 80 | 80 | — | 80 | 80 | — | 80 | 80 |
| Dimethylhexanes | — | 14 | 15 | — | 15 | 14 | — | 15 | 15 |
| Methylheptanes | — | 5 | 4 | — | 4 | 5 | — | 4 | 4 |
| 2,2,5-Trimethylhexane | — | 1 | 1 | — | 1 | 1 | — | 1 | 1 |

What is claimed is:

1. A liquid phase alkylation process which comprises contacting a C$_4$ to C$_6$ isoparaffin or mixtures thereof with an olefin selected from the group consisting of C$_2$ to C$_5$ monoolefins or mixtures thereof at a reaction temperature of between about 80° C and about 225° C and with a catalyst composition comprising a solid perfluorinated polymer catalyst supported on an inert porous carrier having an average pore diameter of between about 50 Å and about 600 Å in a weight ratio of catalyst to support of between about 0.5:100 and about 20:100 wherein said catalyst contains a repeating structure selected from the group of:

a) 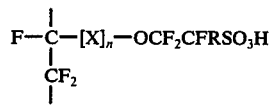

or b) 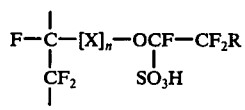

where $n$ is 0, 1 or 2; R is a radical selected from the group consisting of fluorine and perfluoroalkyl radicals having from 1 to 10 carbon atoms; and X is selected from the group consisting of:

where $m$ is an integer from 2 to 10 and Y is a radical selected from the class consisting of fluorine and the trifluoromethyl radical.

2. A process according to claim 1 wherein the weight ratio of said isoparaffin to said olefin varies from about 5:1 to about 1000:1.

3. A process according to claim 1 wherein the weight ratio of isoparaffin to olefin varies from about 20:1 to about 60:1 and the reaction temperature is from about 80° C to about 130° C.

4. A process according to claim 1 wherein the weight hourly space velocity, defined as the weight per hour of olefin divided by the weight of catalyst (not including support) employed, varies from between about 0.5 to about 10.0 hr$^{-1}$.

5. A process according to claim 1 wherein said carrier is selected from the group consisting of alumina, silica, silica-alumina and porous glass.

6. A process according to claim 5 wherein said carrier is silica.

7. A process according to claim 1 wherein said catalyst has the general structure

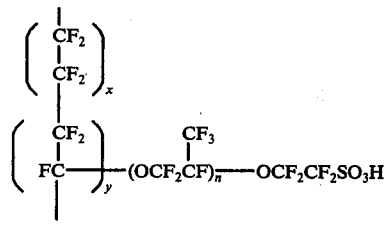

where $n$ equals 1 or 2 and the ratio of $x$ over $y$ varies from about 2 to about 50.

8. A process according to claim 1 wherein said carrier is polytetrafluoroethylene.

* * * * *